United States Patent [19]
Groth et al.

[11] Patent Number: 5,773,630
[45] Date of Patent: Jun. 30, 1998

[54] PROCESS FOR THE PREPARATION OF N-SUBSTITUTED CYCLIC IMIDES

[75] Inventors: Torsten Groth, Köln; Karl-Erwin Piejko, Bergisch Gladbach; Winfried Joentgen, Köln; Josef Käsbauer, Wermelskirchen; Bernd Alig, Königswinter; Werner Strüver, Leverkusen, all of Germany

[73] Assignee: Bayer Aktiengesellschaft, Leverkusen, Germany

[21] Appl. No.: 595,982

[22] Filed: Feb. 6, 1996

[30] Foreign Application Priority Data

Feb. 13, 1995 [DE] Germany ............... 195 04 623.4

[51] Int. Cl.⁶ ................................. C07D 207/36
[52] U.S. Cl. .................... 548/545; 548/407; 548/548; 548/549
[58] Field of Search ............... 548/407, 545, 548/548, 549

[56] References Cited

U.S. PATENT DOCUMENTS 3,890,270  6/1975  Minieri .
4,904,803  2/1990  Fujita et al. .
5,136,052  8/1992  Van Gysel et al. .

FOREIGN PATENT DOCUMENTS 0165574  12/1985  European Pat. Off. .
0177031   4/1986  European Pat. Off. .
0461096  12/1991  European Pat. Off. .
2100800   7/1971  Germany .
1041027   9/1966  United Kingdom .

OTHER PUBLICATIONS

Patent Abstracts of Japan, vol. 17, No. 361, abstract of JP 05–051,362, (1993).
Chemical Abstracts, vol. 75, abstract No. 118127y, abstract of DE 2,100,800, (1971).

*Primary Examiner*—Jacqueline Haley
*Attorney, Agent, or Firm*—Sprung Horn Kramer & Woods

[57] ABSTRACT

N-Substituted cyclic imides are obtained by reacting a cyclic acid anhydride with an amine in the presence of a solvent and an acid catalyst at 80° to 200° C. and with removal of the water formed, it being particularly advantageous to carry out this reaction in the presence of a stabilizer and an inert, dipolar aprotic cosolvent, optionally to add an inert organic solvent of low or zero polarity to the reaction mixture present after the reaction, to add a non-aqueous base in an amount of 0.5 to 50% by weight, based on the cyclic anhydride of the formula (II) used, and to separate off the precipitate formed to give a filtrate containing the N-substituted cyclic imide.

11 Claims, No Drawings

PROCESS FOR THE PREPARATION OF N-SUBSTITUTED CYCLIC IMIDES

BACKGROUND OF THE INVENTION

The present invention relates to a particularly advantageous process for the preparation of N-substituted cyclic imides which can be used for the manufacture of heat-stable plastics and as intermediates for pharmaceuticals and plant protection agents.

It has long been known that N-substituted cyclic imides can be prepared by reacting a cyclic acid anhydride with a primary amine in the presence of an acid catalyst. The reaction mixtures can be worked up by the addition of acids and subsequent washing with water (see e.g. EP-A 165 574), this method naturally leading to organically contaminated waste waters which have to be disposed of.

U.S. Pat. No. 4,904,803 describes a method of working-up in which the reaction mixture is washed first with an aqueous base and then with an aqueous acid. This aqueous working-up is only possible if the reaction has previously been carried out in the presence of copper or copper compounds. The waste waters from this process are not only organically contaminated but also contaminated with copper, creating appreciable problems. According to our own studies, the use of aqueous bases is accompanied by partial hydrolysis of the imides formed, which results in losses of yield and produces waste waters with higher organic contents.

According to U.S. Pat. No. 5,136,052, the reaction mixture is diluted, precipitates formed are filtered off and the filtrate is distilled. Although this process is carried out under anhydrous conditions, it is necessary to remove adhering product from the distillation residue by extraction with solvents and recycle it into the process, which is complicated in terms of process engineering. In particular, large amounts of filtration and distillation residues are obtained and many cost-intensive, individual process engineering operations have to be performed, which has a very unfavourable influence on the costs. Also, the attainable yields are low.

Finally, it is known from GB-B 1 041 027 that N-(2-chlorophenyl)-maleimide is obtained in a yield of only 33% of theory by reacting maleic anhydride with o-chloroaniline in the absence of an acid catalyst and working up the reaction mixture with the addition of sodium bicarbonate (see Example 31 of said patent).

There is still therefore a need for a process for the preparation of N-substituted cyclic imides wherein, as far as possible, the latter are obtained at one and the same time without waste waters, in a simple manner as regards process engineering, in high yields, in high purities and inexpensively. High purities are necessary for a large number of N-substituted cyclic imides if they are to be used for the preparation of copolymers.

SUMMARY OF THE INVENTION

A process has now been found for the preparation of N-substituted cyclic imides of the formula (I):

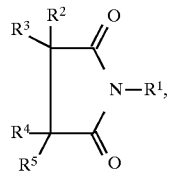

in which
R$^1$ is a C$_1$–C$_{20}$-alkyl, C$_3$–C$_8$-cycloalkyl, C$_3$–C$_{12}$-alkenyl, C$_7$–C$_{12}$-aralkyl or C$_6$–C$_{10}$-aryl radical, each of which can optionally be substituted, or a nitrile group and
R$^2$, R$^3$, R$^4$ and R$^5$ independently of one another are each hydrogen, a C$_1$–C$_{12}$-alkyl or C$_2$–C$_{12}$-alkenyl radical, each of which can optionally be substituted, or a halogen, it also being possible for R$^2$ and R$^3$ together to be C$_1$–C$_6$-alkylene which can optionally be substituted, and for R$^3$ and R$^4$ together to be a covalent bond,
with the proviso that at least one of the following three conditions is satisfied:
a) R$^2$ and R$^3$ together are C$_1$–C$_6$-alkylene which can optionally be substituted,
b) R$^3$ and R$^4$ together are a covalent bond and
c) at least one of the radicals R$^2$ to R$^5$ is C$_2$–C$_{12}$-alkenyl,
wherein a cyclic acid anhydride of the formula

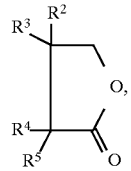

in which
R$^2$ to R$^5$ are as defined for the formula (I),
phthalic anhydride or a partially or completely hydrogenated phthalic anhydride is reacted with an amine of the formula

in which
R$^1$ is as defined for the formula (I),
in the presence of a solvent and an acid catalyst, at 80° to 200° C. and with removal of the water formed, characterized in that the molar ratio of acid anhydride (II) to amine (III) is adjusted to 0.5–5:1 and the process is carried out in the presence of a stabilizer and an inert, dipolar, aprotic cosolvent, an inert organic solvent of low or zero polarity is optionally added to the reaction mixture present after the reaction, a non-aqueous base is added in an amount of 0.5 to 50% by weight, based on the cyclic anhydride of the formula (II) used, and the precipitate formed is separated off to give a filtrate containing the product of the formula (I).

DETAILED DESCRIPTION OF THE INVENTION

Examples of suitable substituents for all alkyl, cycloalkyl, aralkyl, aryl, alkenyl and alkylene radicals are halogens such as fluorine, chlorine, bromine and/or iodine, and OH, NO$_2$, NH$_2$, CN, COOH, C$_1$–C$_4$-alkyl, C$_1$–C$_4$-alkoxy and/or COOC$_1$–C$_6$-alkyl groups. 1 to 4 such substituents, for example, can optionally be present per molecule of the formula (I), (II) or (III). Trifluoromethyl is mentioned in particular as a substituted alkyl group. Examples of C$_1$–C$_4$-alkyl substituents are isopropyl, isobutyl and tert-butyl.

If other NH$_2$ groups are present in addition to those explicitly indicated in the amine of the formula (III), such additional amino groups can also undergo cyclization with the acid anhydride of the formula (II) to form bisimides or polyimides.

R$^1$ is preferably unsubstituted C$_1$–C$_{20}$-alkyl, C$_3$–C$_6$-cycloalkyl or benzyl, unsubstituted phenyl or phenyl substituted by 1 to 3 substituents from the group comprising C$_1$–C$_4$-alkyl, fluorine, chlorine, nitro, hydroxyl, methoxy, trifluoromethyl, trifluoromethoxy and difluoromethoxy.

If R$^2$ to R$^5$ are halogen, fluorine, chlorine and bromine are preferred, especially chlorine.

Preferably, R$^2$ is hydrogen, C$_1$–C$_4$-alkyl, C$_3$–C$_4$-alkenyl, chlorine or bromine, R$^3$ is hydrogen, R$^4$ is hydrogen, or R$^3$ and R$^4$ together are a covalent bond, and R$^5$ is hydrogen, C$_1$–C$_4$-alkyl, C$_3$–C$_4$-alkenyl, chlorine or bromine, either at least one of the radicals R$^2$ and R$^5$ being C$_3$–C$_4$-alkenyl or R$^3$ and R$^4$ together being a covalent bond. As a further preference, R$^2$ and R$^3$ together are C$_1$–C$_4$-alkylene, R$^4$ is hydrogen and R$^5$ is hydrogen, C$_1$–C$_4$-alkyl, C$_3$–C$_4$-alkenyl, chlorine or bromine.

It is particularly preferable to use the following acid anhydrides of the formula (II): maleic anhydride, monochloromaleic anhydride, itaconic anhydride, citraconic anhydride, chlorosuccinic anhydride, C$_1$–C$_4$-alkylsuccinic anhydride and C$_2$–C$_4$-alkenylsuccinic anhydride. It is also particularly preferable to use the following acid anhydrides: phthalic anhydride, hexahydrophthalic anhydride, 3,4,5,6-tetrahydrophthalic anhydride and cis-1,2,5,6-tetrahydrophthalic anhydride.

It is particularly preferable to use the following amines of the formula (III): aniline, methylamine, ethylamine, tert-butylamine, hexylamine, cyclohexylamine, cyclopropylamine, laurylamine, stearylamine, benzylamine, tert-butylaniline, chloroaniline, dichloroaniline, nitroaniline, aminophenol, anisidine, methylaniline, dimethylaniline, ethyl-methylaniline, trimethylaniline, fluoroaniline, difluoroaniline, dichlorotrifluoromethylaniline, trifluoromethylaniline, trifluoromethoxyaniline, difluoromethoxyaniline, aniline derivatives substituted by C$_1$–C$_4$-alkyl, C$_1$–C$_4$-alkoxy, fluorine, chlorine and/or bromine in the 2-, 4- and 5-position, and phenylenediamine. The following amines of the formula (III) are to be used in particular: aniline, 2-chloroaniline, 2,3-, 2,4-, 2,5- and 2,6-dimethylaniline and 2-ethyl-6-methylaniline.

The molar ratio of acid anhydride of the formula (II) to amine of the formula (III) can be e.g. 0.5:1 to 5:1. It is preferably 0.8:1 to 1.2:1. It is particularly preferable to carry out the reaction with equimolar amounts or a small excess of acid anhydride, e.g. up to 1.1 mol of acid anhydride per mol of amine.

It is particularly preferable to prepare the following N-substituted cyclic imides: N-methylmaleimide, N-ethylmaleimide, N-tert-butylmaleimide, N-hexylmaleimide, N-cyclohexylmaleimide, N-cyclopropylmaleimide, N-laurylmaleimide, N-stearylmaleimide, N-benzylmaleimide, N-phenylmaleimide, N-tert-butylphenylmaleimide, N-chlorophenylmaleimide, N-dichlorophenylmaleimide, N-nitrophenylmaleimide, N-hydroxyphenylmaleimide, N-methoxyphenylmaleimide, N,N-(phenylene)-bis-maleimide, N-methylphenylmaleimide, N-dimethylphenyl-maleimide, N-ethyl-methylphenylmaleimide, N-trimethylphenylmaleimide, N-fluoro- phenylmaleimide, N-difluorophenylmaleimide, N-dichloro-trifluoromethylphenylmaleimide, N-trifluoromethylphenylmaleimide, N-trifluoromethoxymaleimide, N-difluoromethoxyphenylmaleimide, the imides corresponding to the abovementioned 2,4,5-tri-substituted anilines, and the corresponding N-substituted cyclic imides derived from monochloromaleic anhydride, itaconic anhydride, citraconic anhydride, chloro- succinic anhydride, C$_1$–C$_4$-alkylsuccinic anhydride and C$_2$–C$_4$-alkenylsuccinic anhydride. It is very particularly preferable to prepare N-phenylmaleimide, N-2-chlorophenyl-maleimide, 2,3-, 2,4-, 2,5- and 2,6-dimethyl-phenylmaleimide and N-(2-ethyl-6-methylphenyl)-maleimide.

Examples of suitable solvents are inert, water-immiscible, water-insoluble organic solvents with which the water formed can be removed from the reaction mixture at the reaction temperature and which have a low or zero polarity. Suitable examples are benzene, toluene, xylenes, cumene, mesitylene, ethylbenzene, butylbenzene, i-propylmethylbenzene, t-butylbenzene, tetralin, decalin, chlorobenzene, dichlorobenzenes, anisole and tetrachloroethane, as well as any desired mixtures of these solvents.

Examples of suitable inert, dipolar aprotic cosolvents are N-methylpyrrolidone, dioxane, formamide, N-methylformamide, dimethylformamide, dimethylacetamide, tetramethylurea, N-methylcaprolactame, butyrolactone, dimethyl sulphoxide, tetramethylene sulphone, hexamethylphosphorotriamide and ethylene glycol dimethyl and diethyl ether. It is possible to use for example 0.1 to 20% by weight of cosolvent, based on the solvent of low or zero polarity. This amount is preferably 0.5 to 10% by weight, particularly preferably 1.5 to 6% by weight.

Examples of suitable acid catalysts are a very wide variety of organic and inorganic protonic acids and also acidic ion exchangers, particular examples being sulphuric acid, phosphoric acid, polyphosphoric acids, trifluoroacetic acid, trichloroacetic acid, alkylsulphonic acids such as methane-sulphonic acid, arylsulphonic acids such as benzenesulphonic acid, p-toluenesulphonic acid and naphthalenesulphonic acid, and ion exchangers in the H form which can be for example strongly acidic or weakly acidic and gelatinous or macroporous, e.g. acidic ion exchangers obtainable from Bayer AG under the references K 1481, K 2441, K 2641, K 2634, VP OC 1052 and VP OC 1501. Phosphoric acids and ion exchangers have the advantage that they can easily be separated from the reaction mixture and re-used.

The acid catalysts can be used in a commercially available grade, e.g. phosphoric acid as 85% phosphoric acid, and water-containing ion exchangers. Water-containing acid catalysts are conveniently dehydrated under azeotropic conditions prior to the addition of the cyclic acid anhydride of the formula (II).

Acid catalysts can be used for example in amounts of 0.1 to 100% by weight, based on the anhydride of the formula (II) used. This amount is preferably 0.1 to 10% by weight in the case of alkylsulphonic and arylsulphonic acids, 0.5 to 20% by weight in the case of sulphuric acid, 5 to 40% by weight in the case of phosphoric and trihalogenoacetic acids and 10 to 100% by weight in the case of acidic ion exchangers, always based on the anhydride of the formula (II) used.

The process according to the invention is carried out in the presence of stabilizers, which are also called polymerization inhibitors. Examples of polymerization inhibitors are phenol and phenol derivatives such as methoxyphenol, p-tertbutylpyrocatechol, 2,2'-methylene-bis-(4-methyl-6-tert-butyl-phenol) and 2,2'-methylene-bis-(4-methyl-6-cyclohexyl-phenol). Polymerization inhibitors can be used for example in amounts of 0.01 to 5% by weight, based on the anhydride of the formula (II) used. This amount is preferably 0.1 to 2.5% by weight.

The reaction temperature is preferably in the range 100° to 180° C., particularly preferably in the range 110° to 160° C. The pressure is not critical. The process can be carried out-at elevated, reduced or normal pressure. Preferably, the process is carried out at normal pressure and the solvent is chosen so that it boils at the desired reaction temperature.

It is advantageous to take the acid anhydride of the formula (II) together with the solvent, the cosolvent, the stabilizer and the acid catalyst and to meter in the amine of the formula (III). The acid anhydride and the amine initially form the corresponding N-substituted amic acid, which is generally converted rapidly to the corresponding N-substituted imide with the elimination of water. The water formed is continuously removed, e.g. in the form of the azeotrope with the particular solvent used. After separation of the water phase from the azeotrope which has been distilled off, the solvent phase can be recycled into the reaction.

The reaction can also be carried out in a different way from the preferred procedure described above, e.g. by initially forming most or all of the N-substituted amic acid and only then starting to remove water.

The reaction is complete when no more removable water is obtained. It can be advantageous to end the removal of water before the theoretically expected amount of water has been removed. For example, the removal of water can be ended when more than 90% by weight, preferably more than 95% by weight and especially more than 97% by weight of the theoretically expected amount of water has been removed.

If the reaction mixture contains acid catalysts which can easily be separated off, it is advantageous to separate them off before the actual working-up. Acidic ion exchangers can be separated off for example by decantation or filtration; phosphoric acids are generally in the form of a separable lower phase after cooling.

The reaction mixture can be worked up initially by the optional addition of an inert organic solvent of low or zero polarity. Such a dilution is frequently advantageous if the reaction has been carried out in a relatively concentrated mixture, e.g. in a reaction mixture which contains, after completion of the reaction, over 35% by weight of the imide formed. The solvent used for the dilution is preferably the same solvent of low or zero polarity as that used for the reaction. The amount of solvent to be added after the reaction can be e.g. 0 to 200% by weight, based on the reaction mixture. This amount is preferably 10 to 150% by weight, especially 30 to 100% by weight.

An essential feature of the process according to the invention is that a non-aqueous base is added in an amount of 0.5 to 50% by weight, based on the anhydride of the formula (II) used, after reaction of the acid anhydride with the amine and, if appropriate, after dilution of the reaction mixture with the solvent of low or zero polarity. This amount is preferably 1 to 30% by weight, especially 2 to 20% by weight.

Examples of suitable non-aqueous bases are anhydrous organic nitrogen bases, anhydrous ammonium compounds and anhydrous ammonia, but said bases do not have to be absolutely anhydrous. The products marketed as anhydrous grades are generally adequate.

Preferred non-aqueous bases are ammonium carbonate, ammonium hydrogen-carbonate, ammonium carbamate, urea and gaseous ammonia, the latter preferably being in diluted form, e.g. mixed with nitrogen.

It is advantageous to lower the temperature of the reaction mixture, for example to 10° to 90° C., preferably 20° to 80° C., during or after the addition of the non-aqueous base. It is particularly preferable to add the non-aqueous base at 40° to 80° C. and separate off the precipitate formed at 10° to 50° C.

The precipitate formed after the non-aqueous base has been added and the temperature lowered is separated off, e.g. by filtration. The precipitate which has been separated off can optionally be washed, e.g. with a solvent of low or zero polarity, and the wash liquor can then be worked up together with the filtrate.

The N-substituted cyclic imide of the formula (I) prepared can be obtained from the filtrate in a variety of ways. In some cases a sufficiently pure product is already obtained by evaporating the filtrate partially or to dryness, optionally at reduced pressure. It is also possible to work up the filtrate by distillation, the solvent and cosolvent, which can be re-used, generally being obtained first, followed by the N-substituted cyclic imide prepared. The distillation can optionally be carried out in the presence of a polymerization inhibitor, for example one of those described above, and/or in the presence of phosphoric acid. It is preferably carried out in the presence of a polymerization inhibitor and optionally in the presence of phosphoric acid, particularly preferably in the presence of a polymerization inhibitor and phosphoric acid.

Another possible method is first to strip the solvent from the filtrate and then to recrystallize the residue. The filtrate obtained in the recrystallization can optionally be recycled.

It is also possible to conceive of other ways of obtaining the N-substituted cyclic imide prepared.

It is not always necessary to isolate the N-substituted cyclic imide of the formula (I) prepared. In some cases it can also be processed further in the form of the filtrate obtained after addition of the non-aqueous base and after separation of the precipitate formed.

Compared with the state of the art, the process according to the invention has the advantage that the working-up is non-aqueous, so no waste water problems arise in the working-up, especially in the deacidification. Moreover, according to the invention, N-substituted cyclic imides are obtained in high yields and purities and distillation residues do not require after-treatments. The N-substituted cyclic imides prepared according to the invention have a high standard of quality and a greatly suppressed acid content because practically all of the acid catalysts, acid by-products and residual acid anhydride has been separated off. The fact that all these advantages are achieved simultaneously is particularly favourable. N-Substituted cyclic imides prepared according to the invention, especially maleimides, are particularly suitable for the manufacture of heat-stable plastics.

EXAMPLES

Unless indicated otherwise, percentages are by weight.
The following abbreviations are used:
NMP=N-methylpyrrolidone
NPMI=N-phenylmaleimide Example 1

1940 g of toluene were refluxed in a water separator together with 120 g of NMP, 926 g of maleic anhydride, 9 g of p-toluenesulphonic acid hydrate and 1.8 g of p-methoxyphenol. 838 g of aniline were metered into the reaction mixture over 10 hours, the water of reaction formed being distilled off azeotropically. The formation and separation of a total of 180 g of water of reaction was complete after a further 4 hours.

The reaction mixture was diluted with 3864 g of toluene, 50 g of solid ammonium carbonate were added at 60° C. and the resulting mixture was stirred for 1.5 hours. After cooling to 30° C., the precipitate formed was filtered off and washed with 460 g of toluene. The filtrates were combined (7696 g) and distilled under vacuum after the addition of 4.5 g of 85% phosphoric acid and 1.5 g of a polymerization inhibitor (Vulkanox® ZKF). The following Fractions were obtained:

| | | |
|---|---|---|
| 1. | 6066 g | of toluene (was re-used in the next batch) |
| 2. | 287 g | of NMP/NPMI mixed Fraction (was re-used in the next batch) |
| 3. | 1178 g | of NPMI with a content of 99.4% by weight (HPLC analysis). |

This corresponded to a yield of 75.1% of theory, based on the aniline used. The acid number was less than 0.1 mg KOH/g NPMI, the melting point was 89.4° C. and the boiling point of Fraction 3 was 140° to 150° C. at 4 mbar. A 47% solution of this NPMI in acrylonitrile was light yellow and clear.

Example 2

Analogous to Example 1 but with recycled toluene and NMP/NPMI from Example 1

2216 g of Fraction 1 from Example 1 were refluxed in a water separator together with the 287 g of Fraction 2 from Example 1, 823 g of maleic anhydride, 9 g of p-toluenesulphonic acid hydrate and 1.8 g of methoxyphenol. 745 g of aniline were metered into the reaction mixture over 9 hours, the water of reaction formed being distilled off. The formation and separation of a total of 157 g of water of reaction was complete after a further 3 hours.

The reaction mixture was diluted with 3583 g of Fraction 1 from Example 1 and otherwise worked up as in Example 1. Distillation gave the following Fractions:

| | | |
|---|---|---|
| 1. | 6021 g | of toluene (was re-used in the next batch) |
| 2. | 307 g | of NMP/NPMI mixed Fraction (was re-used in the next batch) |
| 3 | 1157 g | of NPMI with a content of 99.6% by weight (HPLC analysis). |

This corresponded to a yield of 83.2% of theory. The acid number was 0.1 mg KOH/g NPMI and the melting point and the appearance of the solution in acrylonitrile corresponded to those of the NPMI from Example 1.

Example 3

Analogous to Examples 1 and 2 but with recycled toluene and NMP/NPMI from Example 2

2156 g of Fraction 1 from Example 2 were refluxed in a water separator together with the 307 g of Fraction 2 from Example 2, 823 g of maleic anhydride, 9 g of p-toluenesulphonic acid hydrate and 1.8 g of p-methoxyphenol. The subsequent procedure was as described in Example 2 except that the aniline was added over the course of 10 hours, the formation and separation of the water of reaction was complete after a further 2 hours, a total of 158 g of water of reaction was removed, the reaction mixture was diluted with 2135 g of Fraction 1 from Example 2, the combined filtrates amounted to 6286 g and distillation gave the following Fractions:

| | | |
|---|---|---|
| 1. | 4578 g | of toluene (can be re-used) |
| 2. | 286 g | of NMP/NPMI mixed Fraction (can be re-used) |
| 3. | 1266 g | of NPMI with a content of 99.5% by weight (HPLC analysis). |

This corresponded to a yield of 90.9% of theory. The acid number was 0.5 mg KOH/g NPMI, the melting point was 89.2° C. and a 47% strength solution of this NPMI in acrylonitrile was light yellow and clear.

Example 4 (Comparative Example)

Working-up without using ammonium carbonate 1673 g of toluene were refluxed in a water separator together with 60 g of NMP, 926 g of maleic anhydride, 9 g of p-toluenesulphonic acid hydrate and 1.8 g of methoxyphenol. 838 g of aniline were metered into the reaction mixture over 11 hours, the water of reaction formed being distilled off azeotropically. The formation and separation of a total of 180 g of water of reaction was complete after a further 2 hours.

The reaction mixture was diluted with 2215 g of toluene, cooled to 30° C. and subsequently stirred for 1.5 hours. The precipitate formed was filtered off and washed with 300 g of toluene. The filtrates were combined (5630 g) and distilled under vacuum after the addition of 4.5 g of 85% strength phosphoric acid and 1.5 g of Vulcanox® ZKF. The following Fractions were obtained:

| | | |
|---|---|---|
| 1. | 3954 g | of toluene |
| 2. | 237 g | of NMP/NPMI mixed Fraction |
| 3. | 1228 g | of NPMI with a content of 97.1% (HPLC analysis). |

This corresponded to a yield of 76.5% of theory. The acid number was 5.0 mg KOH/g NPMI, the melting point was 89.2° C. and a 47% solution in acrylonitrile was yellow and turbid.

Example 5

With dioxane as cosolvent (instead of NMP)

1900 g of toluene were refluxed in a water separator together with 150 g of dioxane, 926 g of maleic anhydride, 9 g of p-toluenesulphonic acid hydrate and 1.8 g of p-methoxyphenol. 838 g of aniline were metered into the reaction mixture over 13 hours, the water of reaction formed being distilled off azeotropically. The formation and separation of a total of 179 g of water of reaction was complete after a further 5 hours.

The reaction mixture was diluted with 3922 g of toluene, 50 g of solid ammonium carbonate were added at 60° C. and the resulting mixture was subsequently stirred for 1.5 hours. After cooling to 30° C., the precipitate formed was filtered off and washed with 400 g of toluene. The filtrates were combined (7708 g) and distilled under vacuum after the addition of 4.5 g of 85% phosphoric acid and 1.5 g of Vulkanox® ZKF. The following Fractions were obtained:

| | | |
|---|---|---|
| 1. | 6246 g | of toluene/dioxane mixed Fraction |
| 2. | 1360 g | of NPMI with a content of 98.8% (HPLC analysis). |

This corresponded to a yield of 86.3% of theory. The acid number was less than 0.1 mg KOH/g NPMI, the melting point was 89.6° C. and a 47% solution in acrylonitrile was light yellow and clear.

Example 6

With o-toluidine (instead of aniline)

1308 g of toluene were refluxed in a water separator together with 80 g of NMP, 823 g of maleic anhydride, 8 g of p-toluenesulphonic acid and 1.8 g of p-methoxyphenol. 857 g of o-toluidine were metered into the reaction mixture over 10 hours, the water of reaction formed being distilled off azeotropically. The formation and separation of a total of 160 g of water of reaction was complete after a further 2 hours.

The reaction mixture was diluted with 2550 g of toluene, 40 g of solid ammonium carbonate were added at 60° C. and the resulting mixture was stirred for 1.5 hours. After cooling to 30° C., the precipitate formed was filtered off and washed with 300 g of toluene. The filtrates were combined (5407 g) and distilled under vacuum after the addition of 4.5 g of 85% phosphoric acid and 1.5 g of Vulkanox® ZKF. The following Fractions were obtained:

| | | |
|---|---|---|
| 1. | 3834 g of | toluene |
| 2. | 308 g of | NMP/N-2-methylphenylmaleimide mixed Fraction |
| 3. | 1161 g of | N-2-methylphenylmaleimide with a content of 99.0% (HPLC analysis). |

This corresponds to a yield of 76.6% of theory, based on the o-toluidine used. The acid number was 0.1 mg KOH/g N-(2-methylphenyl)-maleimide, the melting point was 74.0° C., the boiling point of Fraction 3 was 142°–145° C. at 0.6 mbar and a 47% strength solution in acrylonitrile was light yellow and clear.

The yield can be further increased considerably by re-using Fractions 1 and 2 (see Examples 1 to 3).

Example 7

2-Ethyl-6-methylaniline (instead of aniline)

1415 g of toluene were refluxed in a water separator together with 90 g of NMP, 926 g of maleic anhydride, 9 g of p-toluenesulphonic acid hydrate and 1.8 g of p-methoxyphenol. 1217 g of 2-ethyl-6-methylaniline were metered into the reaction mixture over 8 hours, the water of reaction formed being distilled off azeotropically. The formation and separation of a total of 185 g of water of reaction was complete after a further 1.5 hours.

The reaction mixture was diluted with 2540 g of toluene, 30 g of solid ammonium carbonate were added at 60° C. and the resulting mixture was stirred for 1.5 hours. After cooling to 30° C., the precipitate formed was filtered off and washed with 300 g of toluene. The filtrates were combined (6251 g) and distilled under vacuum after the addition of 4.5 g of 85% phosphoric acid and 1.5 g of Vulkanox® ZKF. The following Fractions were obtained:

| | | |
|---|---|---|
| 1. | 4228 g | of toluene |
| 2. | 329 g | of NMP/N-(2-ethyl-6-methylphenyl)-maleimide mixed Fraction |
| 3. | 1633 g | of N-(2-ethyl-6-methylphenyl)-maleimide with a content of 97.8% (HPLC analysis). |

This corresponded to a yield of 82.5% of theory, based on the 2-ethyl-6-methylaniline used. The acid number was 0.2 mg KOH/g N-(2-ethyl-6-methylphenyl)-maleimide, the melting point was 85.9° C., the boiling point of Fraction 3 was 148°–153° C. at 1 mbar and a 47% solution in acrylonitrile was light yellow and clear.

The yield can be further increased considerably by re-using Fractions 1 and 2 (see Examples 1 to 3).

Example 8

With a strongly acidic ion exchanger (instead of p-toluenesulphonic acid)

1893 g of toluene were refluxed in a water separator together with 151 g of NMP, 757 g of maleic anhydride, 436 g of anhydrous ion exchanger VP OC 1052 in the H form (Bayer AG) and 1.5 g of p-methoxyphenol. 698 g of aniline were metered into the reaction mixture over 6.5 hours, the water of reaction formed being distilled off. The formation and separation of a total of 146 g of water of reaction was complete after a further 8.5 hours.

2403 g of the reaction mixture were decanted from the sedimented ion exchanger and the remaining 1338 g of the reaction mixture containing ion exchanger were re-used in the next batch. The reaction mixture which had been separated off was diluted with 2300 g of toluene, 20 g of solid ammonium carbonate were added at 60° C. and the resulting mixture was stirred for 1.5 hours. After cooling to 30° C., the precipitate formed was filtered off and washed with 170 g of toluene. The filtrates were combined (4808 g) and distilled under vacuum.

The following Fractions were obtained:

| | | |
|---|---|---|
| 1. | 3882 g | of toluene (was re-used in the next batch) |
| 2. | 117 g | of NPMI-containing mixed Fraction (was re-used in the next batch) |
| 3. | 706 g | of NPMI with a content of 98.5% (HPLC analysis). |

This corresponded to a yield of 53.5% of theory. The acid number was 0.2 mg KOH/g NPMI, the melting point was 89.4° C., the boiling point of Fraction 3 was 137° to 143° C. at 4 mbar and a 47% strength solution in acrylonitrile was light yellow and clear.

Example 9

Analogous to Example 8 but with recycled toluene, NMP/NPMI mixed Fraction and reaction mixture containing ion exchanger from Example 8

1338 g of reaction mixture containing ion exchanger from Example 8 were refluxed in a water separator together with 1552 g of Fraction 1 from Example 8, 117 g of Fraction 2 from Example 8, 606 g of maleic anhydride and 1.2 g of methoxyphenol. 559 g of aniline were metered into the reaction mixture over 7 hours, the water of reaction formed being distilled off. The formation and separation of a total of 116 g of water of reaction was complete after a further 8 hours.

2657 g of the reaction mixture were decanted from the sedimented ion exchanger and diluted with 2926 g of Fraction 1 from Example 8, 20 g of solid ammonium carbonate were added at 60° C. and the resulting mixture was stirred for 1.5 hours. After cooling to 30° C., the precipitate formed was filtered off and washed with 170 g of toluene. The filtrates were combined (5677 g) and distilled under vacuum with the addition of 1 g of Vulcanox® ZKF. The following Fractions were obtained:

| | | |
|---|---|---|
| 1. | 4570 g | of toluene (was re-used in the next batch) |
| 2. | 121 g | of NPMI-containing mixed Fraction (was re-used in the next batch) |
| 3. | 902 g | of N-phenylmaleimide with a content of 98.9% (HPLC analysis). |

This corresponded to a yield of 85.8% of theory. The acid number was 0.2 mg KOH/g NPMI, the melting point was 89.5° C., the boiling point of Fraction 3 was 137° to 143° C. at 4 mbar and a 47% solution in acrylonitrile was light yellow and clear.

Examples 10 to 13

Examples 10 to 13 were carried out analogously to Example 9, i.e. using toluene, NMP/NPMI mixed Fraction and reaction mixture containing ion exchanger from the previous Example in each case.

The initial amounts of maleic anhydride, methoxyphenol, aniline, ammonium carbonate and Vulkanox® ZKF corresponded to those in Example 9. Prior to vacuum distillation, 3 g of 85% phosphoric acid were also added to the combined filtrates.

The following results were obtained:

Table for Examples 10 to 13

| | Example no. | | | |
|---|---|---|---|---|
| | 10 | 11 | 12 | 13 |
| NPMI (g) | 987 | 974 | 963 | 994 |
| Content according to HPLC analysis (%) | 99.5 | 98.5 | 99.1 | 98.9 |
| Yield (% of theory) | 94.5 | 92.3 | 91.8 | 94.8 |
| Acid number (mg KOH/g NPMI) | 0.2 | 0.2 | 0.2 | 0.2 |
| Melting point (°C.) | 89.4 | 89.7 | 89.7 | 89.6 |
| 47% strength solution in acrylonitrile | always light yellow and clear | | | |

Example 14 (for comparison)

Working-up without using ammonium carbonate 865 g of toluene were refluxed in a water separator together with 64 g of NMP, 257 g of maleic anhydride, 140 g of anhydrous ion exchanger VP OC 1052 (Bayer AG) in the H form and 0.5 g of p-methoxyphenol. 233 g of aniline were metered into the reaction mixture over 4 hours and the water of reaction formed was distilled off. The formation and separation of a total of 51 g of water of reaction was complete after a further 2 hours.

1034 g of the reaction mixture were decanted so as to leave the whole of the ion exchanger in the residual reaction mixture. The decanted reaction mixture was distilled under vacuum, without the addition of further toluene and without the addition of ammonium carbonate, to give 309 g of NPMI with a content of 97.6% (HPLC analysis). This corresponded to a yield of 69.6% of theory. The acid number was 4.8 mg KOH/g NPMI, the melting point was 88.9° C. and a 47% solution in acrylonitrile was light yellow and turbid.

Example 15

With phosphoric acid (instead of p-toluenesulphonic acid)

1800 g of toluene were refluxed in a water separator together with 200 g of NMP, 823 g of maleic anhydride, 170 g of anhydrous phosphoric acid and 1.6 g of p-methoxyphenol. 745 g of aniline were metered into the reaction mixture over 13 hours, the water of reaction formed being distilled off azeotropically. The formation and separation of a total of 149 g of water of reaction was complete after a further 2 hours.

After cooling to 60° C., 3202 g of reaction mixture were decanted. 341 g of reaction mixture, which contained the phosphoric acid catalyst, remained in the reactor and were re-used in the next batch. The decanted reaction mixture was diluted with 3300 g of toluene, 40 g of solid ammonium carbonate were added at 60° C. and the resulting mixture was stirred for 2 hours. After cooling to 30° C., the precipitate formed was filtered off and washed with 300 g of toluene. The filtrates (6707 g) were combined and distilled under vacuum after the addition of 4.0 g of 85% phosphoric acid and 1.5 g of Vulkanox® ZKF.

The following Fractions were obtained:

| | | |
|---|---|---|
| 1. | 5277 g | of toluene (was re-used in the next batch) |
| 2. | 418 g | of NPMI-containing mixed Fraction (was re-used in the next batch) |
| 3. | 793 g | of NPMI with a content of 97.4% (HPLC analysis). |

This corresponded to a yield of 55.7% of theory. The acid number was 0.3 mg KOH/g NPMI and the melting point was 89.5° C.

Example 16

Analogous to Example 15 but with recycled toluene, NPMI-containing mixed Fraction and catalyst-containing reaction mixture from Example 15

2067 g of Fraction 1 from Example 15 were refluxed in a water separator together with 418 g of Fraction 2 from Example 15, 823 g of maleic anhydride, 341 g of the residual reaction mixture from Example 15 and 1.6 g of p-methoxyphenol. 745 g of aniline were metered into the reaction mixture over 11.5 hours and the water of reaction formed was distilled off azeotropically. The formation and removal of a total of 158 g of water of reaction was complete after a further 4 hours.

After cooling to 60° C., 3931 g of reaction mixture were decanted. 298 g of reaction mixture, containing phosphoric acid, remained in the reactor. The decanted reaction mixture was diluted with 4000 g of a mixture of residual Fraction 1 from Example 15 and toluene, 40 g of solid ammonium carbonate were added at 60° C. and the resulting mixture was stirred for 2 hours. After cooling to 30° C., the precipitate formed was filtered off and washed with 300 g of toluene. The filtrates were combined (8205 g) and distilled under vacuum after the addition of 4.0 g of 85% phosphoric acid and 1.5 g of Vulkanox® ZKF.

The following Fractions were obtained:

| | | |
|---|---|---|
| 1. | 6393 g | of toluene |
| 2. | 370 g | of NPMI-containing mixed Fraction |
| 3. | 1169 g | of NPMI with a content of 98.6% (HPLC analysis). |

This corresponded to a yield of 83.2% of theory. The acid number was 0.1 mg KOH/g NPMI, the melting point was 89.7° C. and a 47% strength solution in acrylonitrile was light yellow and clear.

Example 17

With 2,6-dichloroaniline instead of aniline 384 g of toluene were refluxed in a water separator together with 25 g of NMP, 257 g of maleic anhydride, 2.5 g of p-toluenesulphonic acid hydrate and 0.5 g of p-methoxyphenol. A solution of 406 g of 2,6-dichloroaniline in 135 g of toluene was metered into the reaction mixture over 12 hours, the water of reaction formed being distilled off azeotropically. The formation and separation of a total of 53 g of water of reaction was complete after a further 11 hours.

The reaction mixture was diluted with 500 g of toluene, 11 g of solid ammonium carbonate were added at 60° C. and the resulting mixture was stirred for 2 hours. After cooling to 40° C., the precipitate formed was filtered off and subsequently washed with 300 g of toluene. The filtrates were combined (2080 g). They contained N-(2,6-dichlorophenyl)-maleimide in an amount corresponding to a yield of 92.8% of theory (HPLC analysis; based on dichloroaniline). The N-(2,6-dichlorophenyl)-maleimide was crystallized by Fractional concentration of the filtrates.

The following Fractions were obtained:

| Fraction | 1 | 2 | 3 | Σ Fr. 1–3 |
|---|---|---|---|---|
| Amount (g) | 156.4 | 161.5 | 126.1 | 444.0 |
| Content according to HPLC analysis (%) | 99.3 | 97.1 | 94.9 | — |
| Yield (% of theory, based on 2,6-dichloroaniline) | 25.7 | 25.9 | 19.8 | 71.4 |
| Melting point (°C.) | 135 | 135 | 134 | — |

After the third crystallization, the residual mother liquor still contained product in an amount of 17.6% of theory, and the cosolvent. To avoid losses of yield through isolation and to save cosolvent, the mother liquor can be used in a subsequent batch.

What is claimed is:

1. A process for the preparation of an N-substituted cyclic imide of the formula $$\text{(I)}$$

in which $R^1$ is a $C_1$–$C_{20}$-alkyl, $C_3$–$C_8$-cycloalkyl, $C_3$–$C_{12}$-alkenyl, $C_7$–$C_{12}$-aralkyl or $C_6$–$C_{10}$-aryl radical, each of which can optionally be substituted, or a nitrile group and $R^2$, $R^3$, $R^4$ and $R^5$ independently of one another are each hydrogen, a $C_1$–$C_{12}$-alkyl or $C_2$–$C_{12}$-alkenyl radical, each of which can optionally be substituted, or a halogen, it also being possible for $R^2$ and $R^3$ together to be $C_1$–$C_6$-alkylene which can optionally be substituted, and for $R^3$ and $R^4$ together to be a covalent bond, with the proviso that at least one of the following three conditions is satisfied:

a) $R^2$ and $R^3$ together are $C_1$–$C_6$-alkylene which can optionally be substituted, b) $R^3$ and $R^4$ together are a covalent bond and c) at least one of the radicals $R^2$ to $R^5$ is $C_2$–$C_{12}$-alkenyl, wherein a cyclic acid anhydride of the formula $$\text{(II)}$$

in which $R^2$ to $R^5$ are as defined for the formula (I), is reacted with an amine of the formula $$H_2N—R^1 \quad \text{(III)},$$

in which $R^1$ is as defined for the formula (I), in the presence of a solvent and an acid catalyst, at 80° to 200° C. and with removal of the water formed, wherein the molar ratio of acid anhydride (II) to amine (III) is adjusted to 0.5–5:1 and the process is carried out in the presence of a stabilizer and an inert, dipolar, aprotic cosolvent, an inert organic solvent of low or zero polarity is optionally added to the reaction mixture present after the reaction, a non-aqueous base is added in an amount of 0.5 to 50% by weight, based on the cyclic anhydride of the formula (II) used, and the precipitate formed is separated off to give a filtrate containing the product of the formula (I).

2. The process of claim 1, wherein in the formulae (I), (II) and (III), alkyl, cycloalkyl, aralkyl, aryl, alkenyl and alkylene radicals are substituted by one or more fluorine, chlorine, bromine, iodine or OH, $NO_2$, $NH_2$, CN, COOH, $C_1$–$C_4$-alkyl, $C_1$–$C_4$-alkoxy or $COOC_1$–$C_6$-alkyl groups.

3. The process of claim 2, wherein in the formulae (I) and (III), $R^1$ is unsubstituted $C_1$–$C_{20}$-alkyl, $C_3$–$C_6$-cycloalkyl or benzyl, unsubstituted phenyl or phenyl substituted by 1 to 3 substituents selected from the group consisting of $C_1$–$C_4$-alkyl, fluorine, chlorine, nitro, hydroxyl, methoxy and trifluoromethyl, and wherein in the formula (I) and (II), $R^2$ is hydrogen, $C_1$–$C_4$-alkyl, $C_3$–$C_4$-alkenyl, chlorine or bromine, $R^3$ is hydrogen, $R^4$ is hydrogen, or $R^3$ and $R^4$ together are a covalent bond, and $R^5$ is hydrogen, $C_1$–$C_4$-alkyl, $C_3$–$C_4$-alkenyl, chlorine or bromine, either at least one of the radicals $R^2$ and $R^5$ being $C_3$–$C_4$-alkenyl or $R^3$ and $R^4$ together being a covalent bond, or $R^2$ and $R^3$ together being $C_1$–$C_4$-alkylene, $R^4$ being hydrogen and $R^5$ being hydrogen, $C_1$–$C_4$-alkyl, $C_3$–$C_4$-alkenyl, chlorine or bromine.

4. The process of claim 1, wherein the solvents used are benzene, toluene, xylenes, cumene, mesitylene, ethylbenzene, butyl-benzene, i-propylmethylbenzene, t-butylbenzene, tetralin, decalin, chlorobenzene, dichlorobenzenes or anisole, as well as any desired mixtures of these solvents with one another, with the addition of 0.1 to 20% by weight of a cosolvent selected from N-methylpyrrolidone, dioxane, formamide, N-methylformamide, dimethylformamide, dimethylacetamide, tetramethylurea, N-methylcaprolactone, butyrolactone, dimethyl sulphoxide, tetramethylene sulphone, hexamethylphosphorotriamide and ethylene glycol dimethyl and diethyl ether.

5. The process of claim 1, wherein the acid catalyst used is sulphuric acid, phosphoric acid, polyphosphoric acids, trifluoroacetic acid, trichloroacetic acid, alkylsulphonic acids, arylsulphonic acids or an ion exchanger in the H form or a plurality of several of them in an amount of 0. 1 to 100% by weight, based on the anhydride of the formula (II) used.

6. The process of claim 1, wherein the stabilizer used is phenol or a phenol derivative in an amount of 0.01 to 5% by weight, based on the anhydride of the formula (II) used.

7. The process of claim 1, wherein the non-aqueous base used is an anhydrous organic nitrogen base, an anhydrous ammonium compound or anhydrous ammonia in an amount of 0.5 to 50% by weight, based on the anhydride of the formula (II) used.

8. The process of claim 1, wherein the temperature of the reaction mixture is lowered to 10° to 90° C. during or after the addition of the non-aqueous base.

9. The process of claim 1, wherein the N-substituted cyclic imide of the formula (I) prepared is obtained from the filtrate present after the separation of the precipitate formed after the addition of the non-aqueous base, by evaporation, working-up by distillation or stripping of the solvent and recrystallization of the residue.

10. The process of claim 5, wherein the acid catalyst used is an ion exchanger in the H form or phosphoric acid, which are separated from the reaction mixture and re-used.

11. The process of claim 9, wherein the filtrate containing the product of the formula (I) is worked up by distillation and the fractions containing solvent and cosolvent are re-used.

* * * * *

UNITED STATES PATENT AND TRADEMARK OFFICE
CERTIFICATE OF CORRECTION

PATENT NO. : 5,773,630
DATED : June 30, 1998
INVENTOR(S) : Torsten Groth, et al.

It is certified that error appears in the above-indentified patent and that said Letters Patent is hereby corrected as shown below:

Col. 14, Line 18   Delete "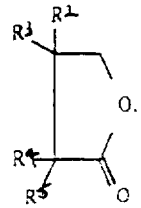"

and substitute 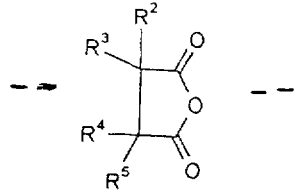

Signed and Sealed this

Twenty-sixth Day of October, 1999

Attest:

Q. TODD DICKINSON

Attesting Officer          Acting Commissioner of Patents and Trademarks